US00PP10388P

United States Patent [19]

McCulloch

[11] Patent Number: Plant 10,388

[45] Date of Patent: May 12, 1998

[54] RHODODENDRON PLANT NAMED 'NORTHERN STARBURST'

[75] Inventor: Steven M. McCulloch, Olympia, Wash.

[73] Assignee: Briggs Nursery, Inc., Olympia, Wash.

[21] Appl. No.: 732,139

[22] Filed: Oct. 16, 1996

[51] Int. Cl.[6] ..... A01H 5/00

[52] U.S. Cl. ..... Plt./55

[58] Field of Search ..... Plt./55, 56, 57

[56] References Cited

U.S. PATENT DOCUMENTS

P.P. 9,981 7/1997 Blough et al. ..... Plt./55

OTHER PUBLICATIONS

Paden et al., Doubling Chromosomes with Colchicine Treatment in Vitro as Determined by Chloroplast Number in Epidermal Guard Cells; American Rhododendron Society Journal, 44(3), 1990, 162–167, 1990.

Tolstead et al., Winter–Hardy Tetraploids of *Rhododendron carolinianum* and *Rhododendron racemosum*, and their Tetraploid Hybrids; American Rhododendron Society Journal, 45(2), 1991, 83 & 84, 1991.

Eiselein, A Study of Chromosome Yields and Growth Responses in Colchicine Treated Rhododendrones; American Rhododendron Society Journal, 48(4), 1994, 205–209, 1994.

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

A new and distinct variety of Rhododendron plant which was produced upon exposure to colchicine during tissue culture is provided. The parent of the new variety was an unregistered and unpatented Rhododendron selection available from Briggs Nursery, Inc. under the 'PJM Compact Form' designation. Unlike the parent variety, the new variety is a tetraploid, forms leaves that are heavier in substance, forms thicker stems, and forms substantially larger vivid blossoms of varying shades of lavender/pink that are somewhat lighter in coloration. The new variety continues to exhibit an attractive compact growth habit and is particularly well suited for growing as attractive ornamentation in the landscape.

2 Drawing Sheets

SUMMARY OF THE INVENTION

The new variety of lepidote Rhododendron plant was discovered and selected by me at the tissue culture laboratory of Briggs Nursery, Inc., located at 4407 Henderson Boulevard, Olympia, Wash., U.S.A. During the creation of the new variety of the present invention, a specific plant of the PJM group that was a selection of *Rhododendron dauricum sempervirens*×*Rhododendron carolinianum* marketed by Briggs Nursery, Inc. and designated 'PJM Compact Form' (non-patented in the United States) was exposed to colchicine during tissue culture. More specifically, actively multiplying micropropagnated shoots were exposed for varying times of 24 to 72 hours to a solution containing 0.25 percent colchicine and 2.0 percent dimethylsulfoxide. The shoots were rinsed following such culture and were subcultured in a standard growing medium. A large number of differing plants were produced by such tissue culture. Prior to this research that resulted in the creation of the new variety of the present invention it was recognized that colchicine was capable of inducing a doubling of the chromosomes in some plants, and that this chemical had been used in the past during the creation of some dissimilar tetraploid Rhododendron varieties, including the 'Epoch' variety (non-patented in the United States).

A single plant of the new variety of the present invention was discovered among the resulting plants that was found to be different from its parent in a number of important respects. More specifically, this new plant possessed the following combination of characteristics:

(a) is a tetraploid,
(b) forms leaves that are heavier in substance than those of 'PJM Compact Form'.

(c) forms thicker stems than 'PJM Compact Form'.
(d) forms substantially larger blossoms than 'PJM Compact Form' that are of varying shades of lavendar/pink and are somewhat lighter in coloration, and
(e) exhibits an attractive compact dense upright spreading growth habit.

The blossoms possess good substance and exhibit good lasting qualities during rain and frost. The stems are strong as well as thick. The new variety performs well during container production and requires generally the same pruning and fertilizing culture as other previously available PJM clones. The tetraploid nature of the new variety has been confirmed by the use of flow cytometry carried out at the University of Minnesota, Minnesota Landscape Arboretum.

Prior to the time the research was carried out that created the new variety of the present invention, those skilled in plant technology would not have been able to predict with any level of certainty that it was possible to create by subjection to colchicine during tissue culture a new Rhododendron variety having the presently specified overall combination of characteristics.

The new variety of the present inventions is particularly well suited for growing as attractive ornamentation in the landscape.

The new variety of the present invention has been successfully propagated by stem cuttings and by tissue culture beginning in March, 1992. Such asexual propagation has demonstrated that the unique combination of characteristics has been well established and is transmitted to succesive generations.

The new variety has been named 'Northern Starburst'.

BRIEF DESCRIPTION OF THE PHOTOGRAPHS

The accompanying photographs show typical specimens of the new Rhododendron plant as depicted in color as true as is reasonably possible to make the same in color illustrations of this character. The plant growth habit, size, foliage, and blossom appearance are depicted. The illustrated plants were grown at Olympia, Wash., U.S.A.

FIG. 1 illustrates a specimen of a typical three year-old plant of the new variety that was grown in a greenhouse. The photograph shows during September the appearance of a plant that was produced by tissue culture. The illustrated plant was approximately 18 to 24 inches in height. The attractive compact dense upright spreading growth habit of the new variety is displayed.

FIG. 2 illustrates during mid-March typical specimens of the attractive purple blossoms of the new variety in various stages of maturity.

DETAILED DESCRIPTION

Figure 1:
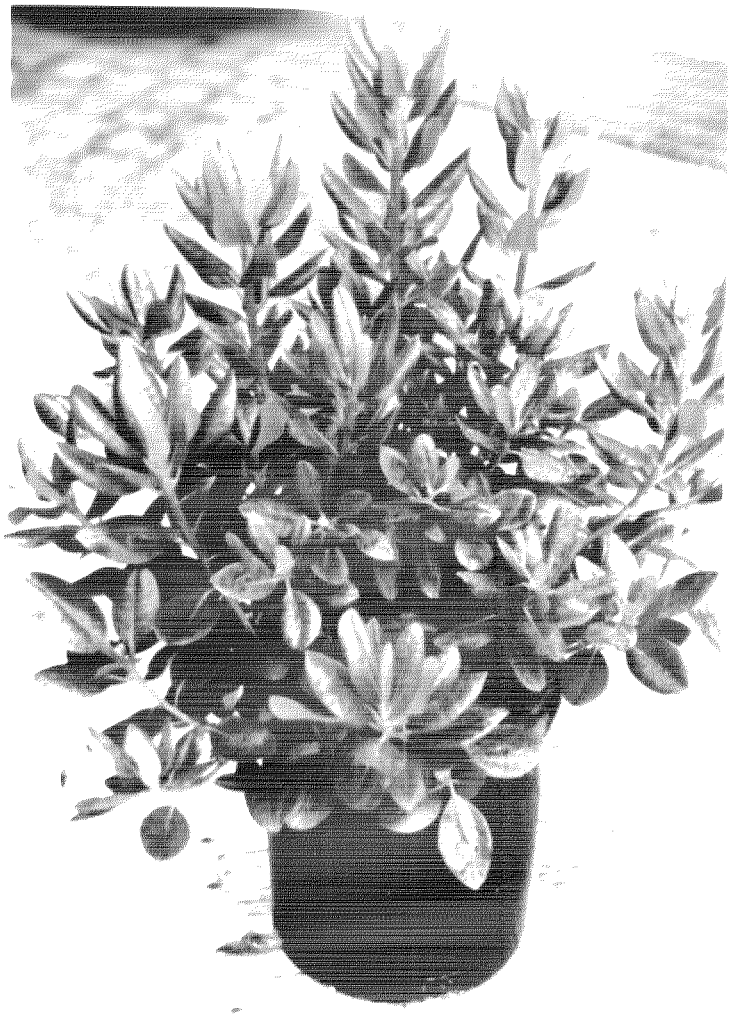
Figure 2:
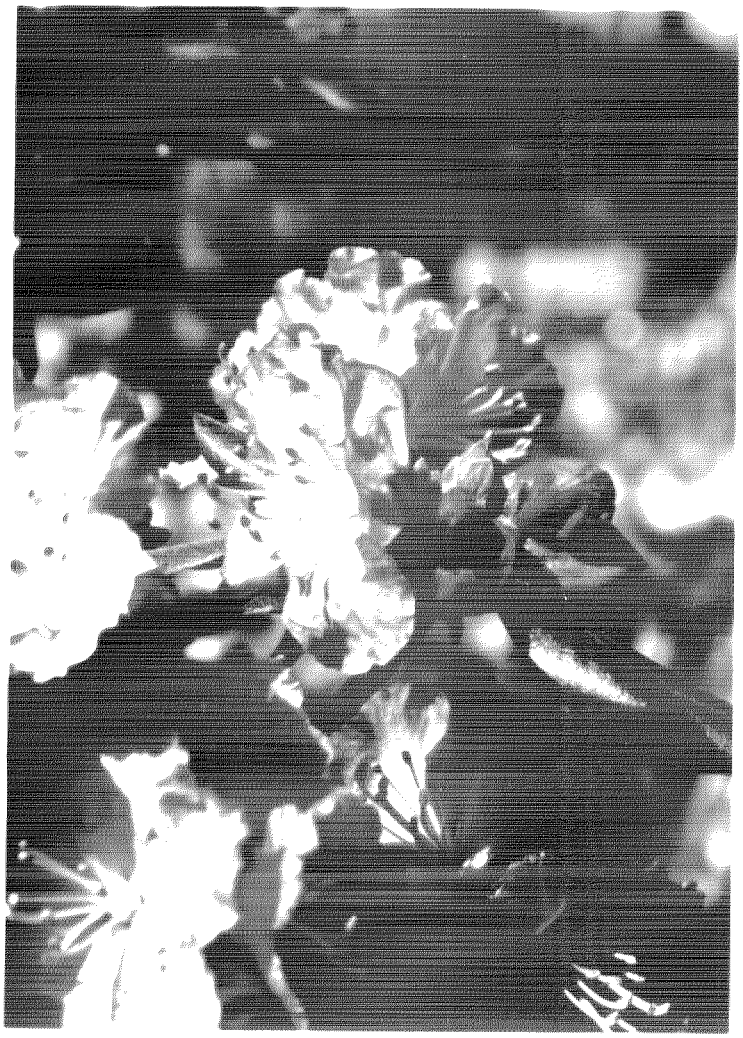

The following is a detailed description of the new Rhododendron variety with color terminology in accordance with The R.H.S. Colour Chart of The Royal Horticultural Society, London, England. The description was prepared following the observation of representative plants of the new variety of the present invention while grown at Olympia, Wash., U.S.A.

Type: Lepidote, broadleaf flowering shrub of *Rhododendron dauricum sempervirens*×*Rhododendron carolinianum*.

Plant Habit: Compact, dense, an upright spreading. The plant commonly is slightly taller than it is broad. Two year-old plants obtained from stem cuttings commonly measure approximately 18 inches in height and approximately 16 inches in width. At seven years of age it is estimated that a plant height of 36 inches will be achieved.

Foliage:

*Shape.*—Broadly elliptic with a broadly acute tip, possess a somewhat oblique base, and are slightly convex.

*Size.*—Approximately 2 to 2.5 inches in length and approximately 1 to 1.25 inches in width.

*Color.*—Mature leaves during the summer growing season commonly approach Green Group 139A (upper surface) and Green Group 139; B (under surface). In the fall the leaf coloration darkness considerably and during the winter assumes a purple-black coloration that approaches Brown Group 200A on the upper surface and assumes a scaly, brownish appearance on the under surface. During the spring the dark leaf coloration gradually changes towards the green coloration of the summer growing season.

*Petioles.*—Commonly approximately 0.25 inch in length, and Yellow-Green Group 144A in coloration.

*Retention.*—The leaves commonly are retained for approximately 1 to 2 years.

Stems:

*Size.*—Thick (as illustrated) and possess a thickness that exceeds that of 'PJM Compact Form'.

Flowers:

*Buds.*—There is ample flower budset at a young age (e.g., on 6 to 8 inch plants).

*Configuration.*—Widely funnel-shaped, and commonly borne a dome-shaped truss with 4 to 5 flowers per truss.

*Size.*—The corolla commonly are aproximately 1.5 inch in length and approximately 2.5 inch in width and consist of five lobes. Each truss commonly is approximately 2.5 inches in height and approximately 4 inches in width. The corolla size is nearly twice that of 'OJM Compact Form'.

*Quantity.*—Moderate.

*Substance.*—Heavier than 'PJM Compact Form'.

*Color.*—The buds commonly are Purple Group 77B and lighten with age. The inner surface of the corolla is Purple Group 77B at the edges with lightening to Purple Group 77C at the center. The outer surface of the corolla tends to more uniformly Purple Group 77B and tends to lighten less than the inner surface upon the passage of time.

*Pedicel.*—Approximately 0.5 inch in length and Yellow-Green Group 144D in coloration.

*Fragrance.*—Lacking.

*Stamens.*—Curved, generally of uneven heights, and commonly approximately 10 in number.

*Pistils.*—Curved and Purple Group 77D in coloration.

Blooming period: Mid-March at Olympia, Wash., U.S.A.

Hardiness: The plant, including the buds, has satisfactorily withstood temperatures as low as −25° F. Has performed well in field production tests for growth and hardiness performed in northern Illinois, U.S.A.

A table is provided below wherein specific characteristics of typical plants of the new 'Northern Starburst' cultivar and of the parent 'PJM Compact Form' cultivar are summarized for ready comparison. The plants were grown in greenhouses at Olympia, Wash., U.S.A.

| Characteristic | 'PJM Compact Form' | 'Northern Starbust' |
|---|---|---|
| Ploidy | Diploid | Tetraploid |
| Leaf Substance | Lighter. | Heavier. |
| Leaf Size | Approximately 1.5 to 2 inches in length and approximately 0.75 to 1 inch in width. | Approximately 2 to 2.5 inches in length and approximately 1 to 1.25 inch in width. |
| Spring Foliage Coloration | Bright apple green. | Bright apple green. |
| Summer Foliage Coloration | Less dramatic. | More gray-green on upper surface due to the presence of discrete hairs that are characteristic of lepidote rhododenrons, and more brown on undersurface because of larger lenticils. |
| Winter Foliage Coloration | Less dramatic and tends to be more purple/maroon. | Deep purple and almost black. |
| Stems | Thinner, approximately 4 mm. in diameter and 12 mm. in circumference. | Thicker, approximately 7 mm. in diameter and 18 mm. in circumference. |
| Interdnode Length | Longer, approximately 0.5 to 0.75 inch. | Shorter, approximately 0.25 to .5 inch. |
| Plant General Appearance | Fine dense appearance due to thinner stems and smaller leaves. | Coarser dense appearance due to thicker stems and larger leaves. |
| Growth Rate | Faster. | Slower. |
| Mature Plant Size | More spreading, and | More upright, and |

-continued

| Characteristic | 'PJM Compact Form' | 'Northern Starbust' |
|---|---|---|
| | commonly exhibits a height of approximately 4 feet and a width of approximately 6 feet. | commonly exhibits a height of approximately 4.5 feet and a width of approximately 4.5 feet. |
| Bloom Time | Mid-March. | Mid-March. |
| Bud Set | More prolific | Less prolific. |
| Bud Size | Approximately 6/16 inch in length and approximately 4/16 inch in width. | Approximately 8/16 inch in length and approximately 6/16 in width. |
| Flowers Per Truss | Approximately 7 to 8. | Approximately 4 to 5. |
| Truss Size | Approximately 2 inches in height and approximately 3 inches in width. | Approximately 2.5 inches in height and approximately 4 inches in width. |
| Blossom Coloration | Darker, and more violet/purple | Light and more lavender/pink. |

I claim:

1. A new and distinct variety of *Rhododendron dauricum sempervirens*×*Rhododendron carolinianum* plant characterized particularly as to novelty by the following combination of characteristics:

(a) is a tetraploid;
(b) forms leaves that are heavier in substance than those of 'PJM Compact Form' (non-patented in the United States).
(c) forms thicker stems than 'PJM Compact Form'.
(d) forms substantially larger blossoms than 'PJM Compact Form' that are of varying shades of lavender/pink and are somewhat lighter in coloration, and
(e) exhibits an attractive compact dense upright spreading growth habit;

substantially as illustrated and described.

* * * * *